United States Patent
Schneider

(10) Patent No.: US 10,125,263 B2
(45) Date of Patent: Nov. 13, 2018

(54) SURFACE-MODIFIED PARTICULATE METAL OXIDES

(71) Applicant: Wacker Chemie AG, Munich (DE)

(72) Inventor: Achim Schneider, Burghausen (DE)

(73) Assignee: WACKER CHEMIE AG, Munich (DE)

( * ) Notice: Subject to any disclaimer, the term of this patent is extended or adjusted under 35 U.S.C. 154(b) by 237 days.

(21) Appl. No.: 15/039,305

(22) PCT Filed: Nov. 19, 2014

(86) PCT No.: PCT/EP2014/075012
§ 371 (c)(1),
(2) Date: May 25, 2016

(87) PCT Pub. No.: WO2015/078745
PCT Pub. Date: Jun. 4, 2015

(65) Prior Publication Data
US 2017/0037251 A1    Feb. 9, 2017

(30) Foreign Application Priority Data

Nov. 27, 2013 (DE) .................. 10 2013 224 206

(51) Int. Cl.
| | | |
|---|---|---|
| *C09C 1/30* | (2006.01) | |
| *C09D 11/00* | (2014.01) | |
| *C09C 3/12* | (2006.01) | |
| *C09D 7/63* | (2018.01) | |
| *C07F 7/18* | (2006.01) | |
| *C09J 11/06* | (2006.01) | |
| *B82Y 30/00* | (2011.01) | |

(52) U.S. Cl.
CPC ............ *C09C 1/3081* (2013.01); *C07F 7/188* (2013.01); *C07F 7/1836* (2013.01); *C09C 3/12* (2013.01); *C09D 7/63* (2018.01); *C09D 11/00* (2013.01); *C09J 11/06* (2013.01); *B82Y 30/00* (2013.01); *C01P 2002/86* (2013.01); *C01P 2006/12* (2013.01); *C01P 2006/22* (2013.01)

(58) Field of Classification Search
CPC ........... C09C 1/3081; C09C 3/12; C09D 7/63; C09D 11/00; C07F 7/1836; C07F 7/188; C09J 11/06; C01P 2002/86; C01P 2006/12; C01P 2006/22
USPC ... 106/31.9, 287.12, 287.13, 287.14, 287.16, 106/481
See application file for complete search history.

(56) References Cited

U.S. PATENT DOCUMENTS

| | | | | |
|---|---|---|---|---|
| 5,686,054 A | * | 11/1997 | Barthel ................. | C09C 1/3081 423/335 |
| 8,435,474 B2 | * | 5/2013 | Fomitchev ............ | C09C 1/3081 423/324 |
| 9,617,428 B2 | * | 4/2017 | Schneider ................. | C09C 3/12 |
| 2003/0027896 A1 | * | 2/2003 | Amano ................. | C09C 1/3081 106/481 |
| 2003/0100631 A1 | * | 5/2003 | Barthel ................. | C09C 1/3081 523/216 |
| 2007/0187313 A1 | * | 8/2007 | Ekeroth ................. | B01J 20/103 210/198.2 |
| 2007/0244223 A1 | | 10/2007 | Gottschalk-Gaudig et al. | |
| 2008/0069753 A1 | * | 3/2008 | Floess ................... | C09C 1/3081 423/335 |
| 2010/0021725 A1 | | 1/2010 | Gottschalk-Gaudig | |
| 2010/0196811 A1 | | 8/2010 | Gottschalk-Gaudig et al. | |
| 2010/0263574 A1 | | 10/2010 | Gottschalk-Gaudig et al. | |
| 2014/0303331 A1 | * | 10/2014 | Mariot ................. | C09C 1/3081 525/477 |
| 2015/0079512 A1 | * | 3/2015 | Sanchez Garcia .... | C09C 1/3081 430/108.3 |

FOREIGN PATENT DOCUMENTS

| | | |
|---|---|---|
| DE | 102007033448 A1 | 1/2009 |
| DE | 102007055879 A1 | 6/2009 |
| EP | 1845136 A1 | 10/2007 |
| WO | 2008077814 A2 | 7/2008 |

OTHER PUBLICATIONS

English translation of the International Preliminary Report on Patentability Chapter II, dated Apr. 8, 2016 for PCT/EP2014/075012; 7 pages.*
English translation of the International Search Report , dated May 4, 2015 for PCT/EP2014/075012; 2 pages.*
G.E. Marciel et al., "Characterization of silica-attached systems by 29Si and 13C cross-polarization and magic-angle spinning nuclear magnetic resonance", Journal of Chromatography, 1981, 205, 438ff •.
G. Engelhardt et al., "Structure Investigation of Organosilicon Polymers by Silicon-29 NMR", Polymer Bulletin, 1981, 5, 577ff •.
G.W. Sears et al., "Determination of Specific Surface Area of Colloidal Silica by Titration with Sodium Hydroxide", Analytical Chemistry, 1956, 28, 1981ff•.

* cited by examiner

*Primary Examiner* — Helene Klemanski
(74) *Attorney, Agent, or Firm* — Brooks Kushman P.C.

(57) ABSTRACT

Modified silica having a fraction of at least 15% T1 groups, or a greater fraction of T1 groups as compared to T3 groups, and an extractable content of less than 15 weight percent have a high proportion of surface modifying groups, and exhibit high thickening power in liquid media.

14 Claims, No Drawings

SURFACE-MODIFIED PARTICULATE METAL OXIDES

CROSS REFERENCE TO RELATED APPLICATIONS

This application is the U.S. National Phase of PCT Appln. No. PCT/EP2014/075012 filed Nov. 19, 2014, which claims priority to German Application No. 10 2013 224 206.9 filed Nov. 27, 2013, the disclosures of which are incorporated in their entirety by reference herein.

BACKGROUND OF THE INVENTION

1. Field of the Invention

The invention relates to metal oxides surface-modified with a fraction of at least 15% of T1 groups or a fraction of T1 groups which is greater than the fraction of T3 groups, where the fraction of the modified metal oxides that is extractable with solvents is not more than 15 wt %, and also to a method for producing these metal oxides and to their use as a rheological additive for adjusting the viscosity, yield point, and the shear-thinning and also thixotropic properties in adhesives, sealants, and coating materials such as paints, inks, and varnishes, for example.

2. Description of the Related Art

Particulate metal oxides with organic functionality are commonly used as active fillers for enhancing the mechanical properties of materials which find diverse use. It is possible by this means, for example, to enhance the scratch resistance of coatings such as paints, inks, and varnishes, or to tailor the mechanical properties of adhesives and sealants. Furthermore, however, even in the uncrosslinked state of the matrix systems, the nanostructured fillers fulfill an extremely important function. Thus the dispersions frequently have relatively high viscosities and in many cases in fact have viscoelastic properties. This pseudoplastic behavior plays an important part in particular for the operation of processing the materials in question. Through deliberate chemical surface modification of the particulate fillers it is possible to steer the interactions with the matrix surrounding them and hence to control the viscoelastic behavior of the dispersion.

WO 2008/077814 discloses the production of resin layers with organic functionality on particulate metal oxides of high specific surface area, and discloses the modified particulate metal oxides and their use. A feature of the metal oxides disclosed is a defined silicone resin structure with organic functionality, a spectroscopic analysis of which is given. In examples 1 to 5, the sum of the intensities of the T2 and T3 groups is greater by a factor of at least 5 than the intensity of the T1 groups; in other words, the fraction of T1 groups on the surface of the modified metal oxide, based on the sum of T1+T2+T3, is in all cases below 15% and is lower than the fraction of T3 groups. Correspondingly, the metal oxides are notable for highly crosslinked silicone resin layers and a low thickening effect in a liquid medium. The metal oxides disclosed in specification WO 2008/077814 are therefore particularly suitable for achieving high levels of filling.

Conversely, in comparative examples 6 and 7 of WO 2008/077814, a higher fraction of T1 groups is measured in relation to the sum of all T groups, and for these metal oxides the extractable fraction is high, at 19.5 wt % and 25.1 wt %, respectively. The method described operates with a high deployment of covering agent, as calculated from the amount of covering agent substance used, relative to the surface area of the silica, and being situated within the region of 9 μmol/m². The reaction products resulting from this method, with a low degree of condensation, have a considerable fraction of silicon-containing compounds which in chemical terms are not firmly attached, and this presents a problem for the further use of the surface-treated metal oxides as, for example, in their use as additives for rheology control.

SUMMARY OF THE INVENTION

It is an object of the invention to overcome the disadvantages of the existing state of the art and to provide metal oxides which are distinguished by a very high thickening level and can therefore be used with particularly good effect as an additive for rheology control, and also to provide a method for producing these metal oxides.

These and other objects are achieved through the provision of metal oxides modified with groups selected from one or more of the groups having the general formula $RSi(OX)(OX')O_{1/2}$ (T1), $R'Si(OX'')(O_{1/2})_2$ (T2) and $R''Si(O_{1/2})_3$ (T3), where R, R', R" are an aliphatic or aromatic hydrocarbon radical having 1 to 24 C atoms and X, X' and X" are hydrogen or an aliphatic or aromatic hydrocarbon radical having 1 to 24 C atoms and R, R', R", X, X' and X" may be identical or different, and where the fraction of T1 groups on the surface of the modified metal oxide, based on the sum of T1+T2+T3, is at least 15%, or the fraction of T1 groups on the surface of the modified metal oxide is greater than the fraction of T3 groups on the surface of the modified metal oxide, and where the fraction of the modified metal oxide that is extractable with solvents is not more than 15 wt %.

DETAILED DESCRIPTION OF THE PREFERRED EMBODIMENTS

The particulate nanostructured metal oxides of the invention have trifunctional groups on their surface, where the silicon atom is bonded to three oxygen atoms. This trifunctional unit is also termed a T unit, and embraces T1 groups with the formula $RSi(OX)(OX')O_{1/2}$, T2 groups with the formula $R'Si(OX'')(O_{1/2})_2$ and T3 groups with the formula $R''Si(O_{1/2})_3$. The entirety of the T groups is also designated by the general formula $RSiO_{3/2}$.

The radicals R, R', R" are selected from the group of the monovalent, optionally mono- or polyunsaturated, optionally branched hydrocarbon radicals having 1 to 24 C atoms, which optionally have further heteroatoms and/or functional groups. They are preferably alkyl or aryl radicals such as methyl, ethyl, propyl such as n-propyl or isopropyl, butyl such as n-butyl, isobutyl or tert-butyl, hexyl such as n-hexyl or isohexyl, octyl such as n-octyl or isooctyl, dodecyl, tetradecyl, hexadecyl, octadecyl, phenyl, tolyl such as o-tolyl, m-tolyl or p-tolyl, xylyl, mesityl or naphthyl groups.

The alkyl or aryl radical may, furthermore, also have further heteroatoms or functional groups. Preferred in this context are monovalent organic groups of the general formula $R=(CH_2)_nY$ where n=1 to 24 and the radical Y is selected from a vinyl, acrylate, methacrylate, glycidyloxy, SH or OH group, a primary amine radical $—NH_2$, a secondary amine radical —NHR such as the N-monomethyl, N-monoethyl, N-monopropyl, N-monobutyl, N-cyclohexyl or aniline radicals, a tertiary amine radical $—NR_2$ such as the N,N-dimethyl, N,N-diethyl, N,N-dipropyl, N,N-dibutyl, N,N-methylethyl, N,N-methylpropyl, N,N-ethylpropyl or N,N-methylphenyl radicals, morpholino, pyrrolyl, indolyl, pyrazolyl, imidazolyl or piperidyl radicals, quaternary amine radicals such as the N,N,N-trimethylammonium, N,N,N-triethylammonium or N,N,N-tripropylammonium radicals, phosphonato, —P(O) (OR$^{\#}$)$_2$ (R$^{\#}$ selected from a methyl, ethyl or phenyl group), isocyanate or protected isocyanate group —N(H)C(O)G, where the protecting group G is eliminated on thermal exposure as H-G (H-G=methyl 2-hydroxybenzoate, 2-hydroxypyridine, 1-hydroxymethyl-1,2,4-triazole, N,N-diethylhydroxylamine, 2-butanone oxime, dimethyl malonate, ethyl acetoacetate, diisopropylamine, benzyl-tert-butylamine, tert-butylmethylamine, tert-butylisopropylamine, 2-isopropylimidazole, 3,5-dimethylpyrazole and ε-caprolactam) or dihydro-3-yl-2,5-furandione.

With particular preference R, R' and/or R" are each a tetradecyl, hexadecyl, octadecyl, methacryloyloxypropyl or glycidyloxypropyl group.

The individual radicals X, X' and X" are selected from the groups defined above for R, R', R", or from hydrogen, and may be identical or different. The radicals of the T group that are bonded to oxygen are preferably identical. More preferably the oxygen-bonded radicals of the T group are hydrogen.

T groups on the surface of the metal oxide (having the general formula RSiO$_{3/2}$, see above) may carry different radicals R; for example, two T1 groups bonded to the surface might differ in the length of their C chains. Preferably the surface of the metal oxide is modified exclusively with one kind of the abovementioned groups R.

In the case of a T1 unit (RSi(OX) (OX')O$_{1/2}$), one oxygen atom forms a siloxane bond to another silicon atom, and there is therefore an attachment of the group to the surface of the metal oxide or to a T2 or T3 group. The other two oxygen atoms, with X and X', carry a hydrogen atom or a hydrocarbon radical. A T1 group therefore represents a noncrosslinked end group. In contrast, in the case of T2 groups (R'Si(OX") (O$_{1/2}$)$_2$), there are two O atoms available for the construction of chain structures, and in the case of T3 groups (R"Si(O$_{1/2}$)$_3$) there are three O atoms available for the crosslinking reaction. Correspondingly, a higher fraction of T1 groups, based on the sum of all T groups, on the surface of the metal oxide indicates a lower degree of crosslinking of the T groups. The mol fraction of T1 groups on the surface of the modified metal oxides of the invention, based on the sum of T1+T2+T3, is at least 15%, preferably at least 20%, more preferably at least 30%, or is greater than the fraction of T3 groups. Preferably the fraction of T1 groups, based on the sum of all T groups on the surface of the metal oxide, is less than 100%.

The metal oxides of the invention are notable accordingly for a low degree of condensation of the organosilicon modifying layer. As shown in the examples, they display a high thickening effect in polar organic systems such as epoxy resins, for example.

The fraction of T1 groups on the surface of the metal oxide may be determined for example by $^{29}$Si CP/MAS NMR spectroscopy, as described for example in G. E. Marciel et al. *Journal of Chromatography*. 1981, 205, 438ff. The chemical shift of the signals provides information on the connectivity of the silicon-containing groups associated with the signals, as set out for example in G. Engelhardt et al. *Polymer Bulletin*, 1981, 5, 557ff. On the basis of the chemical shift, the designations T1, T2 and T3 used here can be assigned in each case to silyl groups of the general formulae RSi(OX) (OX')O$_{1/2}$, R'Si(OX")(O$_{1/2}$)$_2$ and R"Si (O$_{1/2}$)$_3$ respectively, where R, R', R", and also X, X' and X" have the definition specified above, X, X' and X" likewise represent a monovalent alkyl or aryl radical or else hydrogen, and the free valences of the groups (expressed in the fraction O$_{1/2}$) are each satisfied as set out above by way of a siloxane bond to further silicon atoms.

The metal oxides of the invention may be selected by way of example from groups 1 to 5 and 13 to 15 of the Periodic Table of the Elements, it being noted that the expression "metal oxide", used for reasons of simplicity, expressly here also includes the oxides of the semimetals of group 14. Preferred for use are trivalent and tetravalent oxides of groups 4, 13 and 14. Especially preferred for use is silica. Silica in the sense of the invention refers to oxo acids of silicon, and encompasses precipitated silica and fumed (pyrogenically prepared) silica. The salts of the acids, referred to as silicates, are not included. With more particular preference the silica comprises fumed silica.

The metal oxides of the invention may have specific surface areas of 1 to 600 m$^2$/g, preferably 40 to 400 m$^2$/g and more preferably 90 to 270 m$^2$/g (determined by the BET method in accordance with DIN 9277/66131 and 9277/66132).

The tamped densities of the metal oxides of the invention may lie in the range from 10 to 200 g/l, preferably 20 to 100 g/l, more preferably 20 to 60 g/l (determined in accordance with DIN EN ISO 787-11).

A feature of the metal oxides of the invention is that the groups introduced by the modification are bonded firmly to the surface of the metal oxide. A firm bond represents effective chemical attachment and is quantified in accordance with the invention through the fraction of the modified metal oxide that is extractable by solvents, amounting to not more than 15 wt %. The extractable fraction is preferably not more than 6 wt %, more preferably not more than 3 wt %, yet more preferably not more than 2 wt %, and, in preferred specific embodiments of the invention, not more than 1 wt %. A suitable method for evaluating the firmness of bonding of a modification is the quantitative determination of extractable silane, i.e., of silane not bonded chemically to the surface of the metal oxide.

Accordingly, the metal oxides of the invention are notable not only for their low degree of condensation of the organosilicon modifying layer but also, at the same time, for the firm chemical bonding of the surface groups to the metal oxide.

A solvent is a substance which is able to dissolve or dilute gases, liquids or solids without there being any chemical reactions between dissolved material and solvating material. The solvent used for investigating the metal oxides of the invention, tetrahydrofuran, also does not part any chemical bonds of the modifying agents to the surface of the metal oxide. The constituents extractable with this solvent are therefore connected to the metal oxide solely by weaker interactions such as, for example, van-der-Waals forces. A low value measured for the extractable fraction points to a better chemical attachment, in other words firmer attachment, of the modifying agent to the surface of the metal oxide.

The metal oxides of the invention preferably feature very largely complete modification of the surface. Complete in this context means that the preferred degree of occupancy is at least 2 μmol/m$^2$ of the surface area of the metal oxide, in other words that at least 2 μmol/m$^2$ of the surface area of the metal oxide are occupied by modifying agent (synonymous with covering agent). A first idea of the degree of modification or occupancy can be derived from the carbon content found; knowing the chemical structure of the modification and the specific surface area of the unmodified metal oxide as measured by the BET method (see above), it is possible to calculate the degree of occupancy in µmol/m² of surface area of the metal oxide. The degree of occupancy of the metal oxides of the invention is 2 to 6, preferably 2 to 4 µmol/m² and more preferably 2.5 to 3.5 µmol/m² of surface area of the metal oxide.

When the stated metal oxide is fumed silica, the degree of modification can be examined as well, for example, by a suitable method for determining the residual silanol content after the modification, by acid-base titration, as described for example in G. W. Sears et al. *Analytical Chemistry* 1956, 28, 1981ff.

Preferred metal oxides of the invention are those which have a residual silanol content of less than 70%, more preferably of less than 40%, and most preferably of less than 25%.

A further subject of the present invention relates to a method for surface-modifying metal oxides, where first of all a metal oxide is mixed intensively with a modifying agent, and then the metal oxide reacts with the modifying agent in a gas phase operation and is subsequently purified to remove excess modifying agent and byproducts,
where the modifying agent is selected from a silane of the general formula $RSiZ_3$, $R_2SiZ_2$ and/or $R_3SiZ$ alone or any desired mixtures thereof,
where Z is a reactive group such as, for example, hydroxyl, halogen, amine radical, $OR^X$, $OC(O)R^X$, $O(CH_2)_mOH$ or $O(CH_2)_mOR^X$, R and $R^X$ are hydrocarbon radicals having 1 to 24 C atoms,
and m is 1-24,
where 0.5 to 7 µmol of modifying agent per m² of specific surface area of the metal oxide to be modified are used for the modification,
and where, in the reaction of the metal oxide with the modifying agent, auxiliary is added in an amount of less than 3 µmol per m² of the surface area of the metal oxide to be modified.

As already observed above for the metal oxides of the invention, it is also the case for $RSiZ_3$ (synonymous with $R^1SiZ^1Z^2Z^3$), $R_2SiZ_2$ (synonymously with $R^2R^3SiZ^4Z^5$) and $R_3SiZ$ (synonymously with $R^4R^5R^6SiZ^6$) that R and Z describe the individual radicals $R^1$ to $R^6$, and also $Z^1$ to $Z^6$. These radicals are selected from the groups defined above for R and Z, and may be identical or different. The groups selected for R and/or Z are preferably identical.

More preferably the covering agent comprises monoalkyltri-alkoxysilanes such as tetradecyl-, hexadecyl-, octadecyl-, methacryloyloxypropyl-, glycidyloxypropyltrimethoxysilane or the corresponding ethoxy derivatives: tetradecyl-, hexadecyl-, octadecyl-, methacryloyloxypropyl- or glycidyloxypropyltriethoxysilane. Furthermore, in a further preferred version of the invention, alkyltrichlorosilanes can be employed, such as tetradecyl-, hexadecyl-, octadecyl-, methacryloyloxypropyl- or glycidyloxypropyltrichlorosilane, for example.

The silicas of the invention may be modified with exclusively one of the abovementioned covering agents, or alternatively a mixture of two or more of the stated covering agents may be used.

In the method, 0.5 to 7 µmol of modifying agent per m² of specific surface area of the metal oxide to be modified, preferably 1 to 5 µmol, more preferably 2 to 4 µmol and most preferably 2.4 to 3.3 µmol of modifying agent per m² of specific surface area of the metal oxide to be modified, are used for the modification.

The surface-modified metal oxide is produced by means of a method wherein the operation of production takes place in separate steps. These steps involve (1) intensive mixing of the metal oxide with the modifying agents (covering), (2) reaction of the metal oxide with the covering agent, and (3) purification of the modified metal oxide to remove excess modifying agent and byproducts.

For the purposes of the invention, the terms "modifying agent" and "covering agent" or "cover agent" are synonyms.

The surface modification (reaction) is preferably carried out preferably in an atmosphere which does not lead to the oxidation of the surface-modified metal oxide, i.e., preferably less than 10 vol % oxygen, more preferably less than 2.5 vol %; optimum results are obtained at less than 1 vol % oxygen.

The pressure during the method steps ranges from a slight subatmospheric pressure of 0.2 bar up to a superatmospheric pressure of 100 bar, with preference being given on technical grounds to standard pressure, meaning unpressurized operation relative to external/atmospheric pressure.

It is possible optionally for a protic solvent to be added. A solvent is referred to as protic if one molecule possesses a functional group from which hydrogen atoms in the molecule can be split off as protons (dissociation). In view of the high polarity of the OH bond it can be split comparatively easily with elimination of a positively charged hydrogen atom, the proton.

The most important protic solvent is water, which dissociates (in simplified terms) into a proton and a hydroxide ion. Examples of other protic solvents include alcohols and carboxylic acids. Protic solvents which can be added in accordance with the invention are, for example, liquid or vaporizable alcohols such as isopropanol, ethanol or methanol, or water. Mixtures of the abovementioned protic solvents as well may be added. Preference is given to adding 1 to 50 wt % of protic solvent, based on the metal oxide, more preferably 5 to 25 wt %. Particularly preferred is the addition of water as a protic solvent.

By adding a relatively large amount of water during the modification, a product is obtained wherein X comprises predominantly hydrogen groups and less frequently alkyl groups.

The modification reaction of the invention takes place in a gas phase operation, meaning that the covering agent is added to the pure, very largely dry (and therefore pulverulent) metal oxide. In a liquid phase operation, in contrast, the metal oxide would be introduced in a liquid phase. The modifying agents (covering agents) are added to the metal oxide preferably in liquid form. The modifying agents here may be admixed in pure form or as solutions in known solvents used industrially, examples being alcohols such as methanol, ethanol, or isopropanol, for example, ethers such as diethyl ether, tetrahydrofuran, or dioxane, for example, or hydrocarbons such as hexanes or toluene, for example. The concentration of the modifying agents in the solution here is 5 to 95 wt %, preferably 30 to 95 wt %, more preferably 50 to 95 wt %.

In accordance with the invention the amounts of the liquid constituents are selected such that the reaction mixture is always a dry powder bed. Dry power bed in this context means that the mixture is present substantially as solid (metal oxide particles) in the gas phase. Liquids are added only in the small quantities in which they are absolutely necessary—for example, as a reactant, as an auxiliary for reducing the reaction temperatures and/or times, or as a solvent for establishing the viscosity needed for the nozzle spraying of other reactants or auxiliaries. This contrasts with the operating regime in the liquid phase, i.e., the reaction of a metal oxide dispersed in a liquid phase.

In order to ensure that the reaction mixture takes the form of a dry powder bed, the amounts by weight of liquid constituents used do not exceed the amount by weight of the metal oxide that is used. Preference is given to using 5 to 50, more preferably 20 to 35, parts by weight of liquid constituents relative to 100 parts of the metal oxide.

Additionally employed for producing the metal oxides of the invention are substances which allow the reaction times needed for reaction of the metal oxide of the modifying agent to be shortened and/or which allow the required operating temperatures to be lowered. These substances are referred to below by the term "auxiliaries". Surprisingly is has been ascertained that the amount of auxiliaries selected can be so low that in the modifying reaction a high fraction of T1 groups on the surface of the modified metal oxide, based on the sum of T1+T2+T3, or a fraction of T1 groups which is greater than the fraction of T3 groups, is generated and the groups at the same time are firmly bonded to the surface of the metal oxide. The fact that effective chemical attachment has taken place may be demonstrated in turn by the fact that the solvent-extractable fraction of the modified metal oxide is low.

Hence the amount of the auxiliary in the method of the invention is up to 3 µmol per $m^2$ of (absolute) surface area of the metal oxide to be modified. Preference is given to using 0.5 to 2.5 µmol of auxiliary per $m^2$ of surface area of the metal oxide to be modified. The absolute surface area of the unmodified metal oxide may be calculated in turn from its mass and from the specific surface area as measured by the BET method (see above).

The auxiliary according to the invention preferably comprises substances which have functional groups giving a basic reaction. They include, for example, hydroxides of alkali metals and alkaline earth metals, such as potassium hydroxide and sodium hydroxide, for example, and also the salts thereof derived from the corresponding alcohols or carboxylic acids, examples being sodium methoxide, sodium ethoxide or sodium acetate. The compounds giving a basic reaction may further be selected from nitrogen-containing compounds such as ammonia or organically substituted primary, secondary or tertiary amines. The monovalent organic substituents of the stated alcohols, carboxylic acids and amines include saturated and unsaturated, branched and also unbranched hydrocarbon radicals, which, furthermore, may also have other heteroatoms or functional groups. The compounds giving a basic reaction may be added as they are or else as a solution in inert or reactive solvents. Preferred for use are aqueous sodium or potassium hydroxide solution, aqueous ammonia solution, isopropylamine, n-butylamine, isobutylamine, tert-butylamine, cyclohexylamine, triethylamine, morpholine, piperidine or pyridine.

By varying the chemical nature of the auxiliary used and also the amount thereof relative to the absolute surface area of the metal oxide used, it is possible to steer the degree of crosslinking of the silicone resin layer within a very broad range. As the examples show, reducing the amount of the auxiliary results in a product having a lower degree of crosslinking, which is also manifested in an increase in the thickening effect of the product. Comparing example 4 with 3, the reduction in the amount of auxiliary, in that case aqueous ammonia solution, resulted in a product having an increased fraction of T1 groups and enhanced thickening effect. This tendency was also observed for other covering agents (example 7 compared with example 6 or example 9 versus 8), and also for another auxiliary, in that case triethylamine (example 11 versus 10).

It was particularly surprising that in this context the use even of significantly substoichiometric amounts of the auxiliary resulted in near-quantitative, chemically firm attachment of the modification to the metal oxide. In contrast, when no auxiliary is used, a significantly increased extractable fraction of 4.9 wt % (example 5) is found in comparison to only around 1 wt % (examples 1-4) when using aqueous ammonia solution as an auxiliary, as manifested, in the case of example 5 relative to example 4, in differences including a comparatively low thickening effect, and with the possibility, as maintained above, to be accompanied by other technical drawbacks as well. Hence the viscosity of the dispersion without addition of auxiliaries is 6.92 Pa·s, whereas on addition of 0.6 µmol of aqueous ammonia solution it is 8.57 Pa·s (example 4). With a decreasing amount of auxiliary from example 3 to example 4, in that case aqueous ammonia solution, an increase in the viscosity is observed.

The covering agents are preferably added in the form of ultrafinely divided aerosol, wherein the aerosol has a settling velocity of 0.1 to 20 cm/s. An aerosol is a mixture (dispersion) of solid or liquid suspended particles and a gas. The covering of the metal oxide with the stated modifying agents is accomplished preferably by nozzle technologies or comparable technologies. Effective jetting technologies may be, for example, jetting in 1-fluid nozzles under pressure (preferably at 5 to 20 bar), jetting in 2-fluid nozzles under pressure (preferably with gas and liquid at 2-20 bar), ultrafine division with atomizers or gas/solid exchange assemblies having movable, rotating or static internals, which allow homogeneous distribution of the covering agents with the pulverulent metal oxide.

The aerosol may be applied via nozzles from above onto the pulverulent solid which has been set in motion, in which case the nozzles are located above the fluid level and are surrounded by the homogeneous gas phase, or may be introduced into the fluidized solid, in which case the metering apertures are located below the fluid level and, accordingly, are surrounded by the heterogeneous particle/gas mixture. Jetting from above is preferred.

The addition of the silanes and of the basic-reacting compounds which function as auxiliary may take place simultaneously or in succession. Preference is given first to homogeneous covering of the metal oxide of the auxiliary, and subsequently to covering with the silane.

The reaction (step 2) takes place preferably at temperatures of 30° C. to 350° C., preferably 40° C. to 250° C., more preferably 50° C. to 150° C. In one preferred version, the reaction step takes place at 100° C. to 120° C. The temperature profile may be kept constant during the reaction or, as described in EP 1 845 136, may have an ascending gradient.

The residence time of the reaction (step 2) is preferably 1 min to 24 h, more preferably 15 min to 300 min, and, for reasons of space-time yield, most preferably 15 min to 240 min.

Covering (1) and reaction (2) take place preferably with mechanical or gasborne fluidization. Whereas in the case of mechanical fluidization the particulate powder is brought into the fluid state by movement of a body (for example, a stirring paddle) in the bed or in the fluid, this is achieved in the case of gasborne fluidization simply by introduction of a gas, preferably from below (e.g., in a fluidized bed). Gasborne fluidization may be accomplished by any inert gases that do not react with the modifying agents, the metal oxide and the modified metal oxide, in other words do not lead to side-reactions, degradation reactions, oxidation events, and flame and explosion phenomena. Used properly here are nitrogen, argon and other noble gases, and also carbon dioxide. The fluidizing gases are supplied preferably in the superficial gas velocities range from 0.05 to 5 cm/s, more preferably from 0.5 to 2.5 cm/s. The term "superficial gas velocity" refers to the ratio of the volume flow rate of the flowing gas, present in the range in which the steps of (1) covering, (2) reaction and/or (3) purification are carried out, and to the free cross-sectional area of the corresponding area through which the flow passes. Particularly preferred is mechanical fluidization, which takes place without additional use of gas beyond the inertization, by means of paddle stirrers, anchor stirrers, and other suitable stirring members.

The purification step (3) is preferably characterized by movement, with slow movement and a low level of mixing being particularly preferred. The stirring members in this case are preferably adjusted and moved in such a way that there is mixing and fluidizing, but not complete vortexing.

During the purifying step for removing unreacted starting materials and also byproducts that have been obtained, the operating temperature may optionally be raised. Purification takes place preferably at a temperature of 100° C. to 350° C., more preferably 105° C. to 180° C., and most preferably, 110° C. to 140° C.

In order to avoid oxidation and to make the purification more effective, the purifying step may also include the supply of relatively large amounts of inert gas, preferably nitrogen, argon, and other noble gases, and also carbon dioxide, corresponding to a superficial gas velocity of preferably 0.001 to 10 cm/s, more preferably 0.01 to 1 cm/s.

Covering, reaction, and purification may be carried out as a batchwise (discontinuous or batch) or a continuous operation. Preferred for technical reasons is a continuous reaction regime of the kind described for example in EP1845136.

Additionally during the modification (i.e., during the covering and/or reaction) or following the purification, it is possible to use continuous or discontinuous methods for the mechanical compaction of the silica, such as, for example, presses, pressing rolls, grinding assemblies, such as edge runner mills or ball mills, compaction by screws or screw mixers, screw compressors, briquetting machines, or compaction by withdrawal of the air or gas content under suction by means of appropriate vacuum techniques.

Particular preference is given to mechanical compaction by pressing rolls, grinding assemblies such as ball mills, screws, screw mixers, screw compressors or briquetting machines during the covering in step (1). Covering and mechanical compaction therefore take place simultaneously in one assembly, this being positive for reasons of space/time yield and for saving on a separate operating step.

In a further particularly preferred procedure, following the purification, methods are employed for the mechanical compaction of the metal oxide, such as compacting by withdrawal of the air or gas content under suction by means of suitable vacuum techniques, or pressing rolls, or combinations of both methods.

Additionally, in one particularly preferred procedure, the metal oxides may be ground following the purification. In this case it is possible to use assemblies such as pinned disk mills, hammer mills, opposed-jet mills, impact mills, or devices for milling/classifying.

A further subject of the invention is the use of the surface-modified nanostructured metal oxides of the invention or of the surface-modified nanostructured metal oxides produced by the method of the invention for controlling the flow properties of media such as adhesives, sealants, and coating materials, for improving the mechanical properties of elastomers, and for controlling the charge and flow properties of powders such as toners or powder coating materials. The metal oxides of the invention are notable for a strongly thickening effect for example in polar organic resins. Use for controlling the rheological properties of liquid media is preferred.

Surprisingly it has been found that the thickening effect of the modified metal oxide, measured as dispersion viscosity, is not lower but instead frequently in fact higher when smaller amounts of auxiliary are added to the method (compare example 4 with 1 to 3, example 7 with 6, and example 9 with 8, in each of which aqueous ammonia solution was the auxiliary added). The same is also true when using triethylamine as auxiliary (compare example 11 with 10).

With the aid of the method of the invention, metal oxides are provided which have a low degree of crosslinking on the surface in conjunction with firm chemical attachment and which therefore, as additive, achieve a good thickening effect in liquid media. The method of the invention furnishes an optimum combination of the reaction parameters such as, for example, the amount of auxiliary used and reaction in the gas phase process, in order to achieve this very high thickening effect in conjunction with effective chemical attachment.

Methods of Analysis:

1. Determination of Carbon Content (% C)

Elemental analysis for carbon took place in accordance with DIN ISO 10694 using a CS-530 elemental analyzer from Eltra GmbH (D-41469 Neuss, Germany).

From the FIGURE obtained it is possible, with knowledge of the type of modification (i.e., knowledge of R from $RSiO_{3/2}$, since it is a determinant of factors including % C and molar mass M), to calculate the occupancy in $\mu mol/m^2$ of the metal oxide, as follows:

$$\text{Occupancy} = 10^6 \times \frac{\% \, C(\exp) \times m(\text{total})}{\% \, C((RSiO)_{3/2}) \times M((RSiO)_{3/2}) \times A_{spec} \times m(\text{metal oxide})}$$

where

% C(exp): experimentally determined carbon content in w % m(total): total mass of the surface-modified metal oxide in g

% $C(RSiO_{3/2})$: carbon content, as computable theoretically from the corresponding empirical formula of the type of modification, of the functional group $RSiO_{3/2}$ in w %

$M(RSiO_{3/2})$: molecular mass of the functional group $RSiO_{3/2}$ in g/mol $A_{spec}$: specific surface area of the metal oxide in $m^2/g$ m(metal oxide): mass of the non-surface-modified metal oxide in g where:

$$m(\text{metal oxide}) = m(\text{total}) \times \left\{ 1 - \frac{\frac{\% \, C(\exp)}{100\%} - \frac{\% \, C(\exp)}{100\%} \times [100\% - \% \, C(RSiO_{3/2})]}{100\%} \right\}$$

For simplification, here, the weight increase associated with the surface modification in the rough approximation m(metal oxide)=m(total) is disregarded, so that the equation simplifies significantly to read:

$$\text{Occupancy} = 10^6 \times \frac{\%\, C(\exp)}{\%\, C((RSiO)_{3/2}) \times M((RSiO)_{3/2}) \times A_{spec}}$$

2. Determination of Residual Amount of Unmodified Silica Silanol Groups

The residual silanol content was determined in analogy to G. W. Sears et al. *Analytical Chemistry* 1956, 28, 1981ff by means of acid-base titration of the silica in suspension in a 1:1 mixture of water and methanol. The titration took place in the region above the isoelectric point and below the pH range of dissolution of the silica.

The residual silanol content in % can be computed accordingly by the following formula:

SiOH=SiOH(silyl)/SiOH(phil)*100% where
SiOH(phil): titration volume from the titration of the untreated silica
SiOH(silyl): titration volume from the titration of the silylated silica 3. Determination of Fraction of Extractable Silylating Agent 2.50 g of the silica for investigation are stirred with a spatula into 47.50 g of tetrahydrofuran in a screw-top PE vessel, and the vessel is then closed. After a resting time of 30 minutes in an ice bath, the mixture is treated for 30 minutes in an ultrasound bath with ice cooling (Sonorex Digitec DT 156, BANDELIN electronic GmbH & Co. KG, D-12207 Berlin, Germany) and then the clear filtrate is obtained by pressure filtration (5 bar nitrogen) through a PTFE membrane filter (pore size: 0.2 μm, diameter: 47 mm, Sartorius AG, Göttingen, Germany). Precisely 10.00 ml of this filtrate are taken off as analysate for determining the silicon content by means of atomic absorption spectroscopy (Atom Absorption Spectrometer 2100, Perkin Elmer Waltham, Mass., USA) and weighed.

The extractable constituents in w % can be calculated as follows:

$$\text{Extractable constituents} = 10^{-4} \times \frac{m(\text{THF}) \times V(\text{analysate})}{m(\text{metal oxide}) \times M(\text{Si})} \times \frac{c(\text{analysate}) \times M(\text{RSiO}_{3/2})}{m(\text{analysate})}$$

where
m(THF): initial mass of tetrahydrofuran (=47.50 g)
V(analysate): volume of the analysate (=10.00 ml)
m(metal oxide): initial mass of the surface-modified metal oxide (=2.50 g)
M(Si): molar mass of silicon (=28.09 g/mol)
c(analysate): silicon content of the analysate in mg/l
m(analysate): final mass of the analysate in g
M(RSiO$_{3/2}$): molecular mass of the functional group RSiO$_{3/2}$ in g/mol 4. Characterization by NMR Spectroscopy $^{29}$Si solid-state NMR spectra were detected by cross polarization and Magic Angle Spinning (CP/MAS) using an AVANCE 400 WB NMR spectrometer (Bruker Corporation, Billerica, Mass., USA) equipped with a 7 mm double resonance MAS probe (field strength 9.4 tesla; resonance frequency for $^{29}$Si 79.51 MHz and 400.23 MHz for $^1$H). A linear ramp of 80-100% was utilized for the proton RF amplitude during the cross polarization (CP) with a MAS rotational frequency of 5 kHz. The contact time was 5 ms. Up to 20,000 scans were recorded with an experimental repetition time of 3 s (further recording parameters: 90° Si pulse=5 μs, TD=1662, SWH=23 809, o1=−5566 Hz, decoupling: TPPM15; processing parameters: SI=16 384; Gaussian multiplication with LB=−5 Hz and GB=0.03). All measurements took place at room temperature. The $^{29}$Si chemical shifts were referenced to tetramethylsilane (TMS)=0 ppm as external reference standard, using octakis(trimethylsiloxy) silsesquioxane ($Q_8M_8$; the most strongly shielded $Q^4$ group is located at −109 ppm relative to TMS).

The relative proportions of the T1, T2 and T3 signals as reported in table 2 were calculated from the signal intensities obtained by deconvolution, in accordance with the following formula:

$$^{29}\text{Si-CP/MAS } Tn = \frac{\text{Int}(Tn)}{\text{Int}(T1) + \text{Int}(T2) + \text{Int}(T3)} \times 100\%$$

where
n=1, 2, 3
Int(T1): intensity of the signal of the T1 group
Int(T2): intensity of the signal of the T2 group
Int(T3): intensity of the signal of the T3 group 5. Investigation of Rheological Behavior of Metal Oxides 3 g each of the reaction products from examples 1 to 9, or 8 g of the reaction products from examples 10 and 11, are incorporated under ambient pressure in a DISPERMAT® vacuum dissolver from VMA-Getzmann GmbH (D-51580 Reichshof, Germany) equipped with a 40 mm dissolver disk within from 1 to 2 minutes at 750 rpm into 97 g, or 92 g for examples 10 and 11, of Epikote RIM135, acquired from Hexion Specialty Chemicals Inc. (Duisburg, Germany), and then are dispersed at 6000 rpm for 5 minutes under a reduced pressure of 0.3 bar.

After a resting time of one hour, the viscosity of the dispersion is measured in rotation by means of an air-cushioned Haake RheoStress 600 rheometer (Thermo Fisher Scientific Inc., Waltham, Mass., USA) with cone/plate geometry (35 mm, 2°) at 25° C. To determine the viscosity, a measuring profile is used in this case which consists of two sections, with shearing taking place first for 120 s at 1 s$^{-1}$ (measuring section 1) and then for a further 120 s at 10 s$^{-1}$ (measuring section 2). The viscosity reported in table 2 was calculated as the average value of the last ten collected data points of the second measuring section.

EXAMPLES

Example 1

Added to 100 g of a hydrophilic silica having a specific surface area of 200 m²/g, determined by the BET method in accordance with DIN 66131 and 66132 (available under the name HDK® N20 from Wacker Chemie AG, Munich, Germany) under a nitrogen atmosphere, by jetting through a two-fluid nozzle (hollow cone nozzle, model 121, from Düsen-Schlick GmbH, D-96253 Untersiemau/Coburg, Germany, 30° spray angle, 0.1 mm bore, operated with 5 bar nitrogen) is a mixture consisting of 1.85 g of ammonia and 3.75 g of water. Added subsequently in a similar way are 21 g of hexadecyltrimethoxysilane (hollow cone nozzle, model 121, from Düsen-Schlick GmbH, D-96253 Untersiemau/Coburg, Germany, 30° spray angle, 0.2 mm bore, operated with 5 bar nitrogen). The reaction mixture is heated at 100° C. for three hours with vigorous stirring, then cooled to room temperature before being analyzed.

The experimental and analytical data are summarized in tables 1 and 2.

Example 2

Added to 100 g of a hydrophilic silica having a specific surface area of 200 m$^2$/g, determined by the BET method in accordance with DIN 66131 and 66132 (available under the name HDK® N20 from Wacker Chemie AG, Munich, Germany) under a nitrogen atmosphere, by jetting through a two-fluid nozzle (hollow cone nozzle, model 121, from Düsen-Schlick GmbH, D-96253 Untersiemau/Coburg, Germany, 30° spray angle, 0.1 mm bore, operated with 5 bar nitrogen) is a mixture consisting of 1.25 g of ammonia and 3.75 g of water. Added subsequently in a similar way are 21 g of hexadecyltrimethoxysilane (hollow cone nozzle, model 121, from Düsen-Schlick GmbH, D-96253 Untersiemau/Coburg, Germany, 30° spray angle, 0.2 mm bore, operated with 5 bar nitrogen). The reaction mixture is heated at 100° C. for three hours with vigorous stirring, then cooled to room temperature before being analyzed.

Example 3

Added to 100 g of a hydrophilic silica having a specific surface area of 200 m$^2$/g, determined by the BET method in accordance with DIN 66131 and 66132 (available under the name HDK® N20 from Wacker Chemie AG, Munich, Germany) under a nitrogen atmosphere, by jetting through a two-fluid nozzle (hollow cone nozzle, model 121, from Düsen-Schlick GmbH, D-96253 Untersiemau/Coburg, Germany, 30° spray angle, 0.1 mm bore, operated with 5 bar nitrogen) is a mixture consisting of 0.66 g of ammonia and 3.75 g of water. Added subsequently in a similar way are 21 g of hexadecyltrimethoxysilane (hollow cone nozzle, model 121, from Düsen-Schlick GmbH, D-96253 Untersiemau/Coburg, Germany, 30° spray angle, 0.2 mm bore, operated with 5 bar nitrogen). The reaction mixture is heated at 100° C. for three hours with vigorous stirring, then cooled to room temperature before being analyzed.

Example 4

Added to 100 g of a hydrophilic silica having a specific surface area of 200 m$^2$/g, determined by the BET method in accordance with DIN 66131 and 66132 (available under the name HDK® N20 from Wacker Chemie AG, Munich, Germany) under a nitrogen atmosphere, by jetting through a two-fluid nozzle (hollow cone nozzle, model 121, from Düsen-Schlick GmbH, D-96253 Untersiemau/Coburg, Germany, 30° spray angle, 0.1 mm bore, operated with 5 bar nitrogen) is a mixture consisting of 0.22 g of ammonia and 3.75 g of water. Added subsequently in a similar way are 21 g of hexadecyltrimethoxysilane (hollow cone nozzle, model 121, from Düsen-Schlick GmbH, D-96253 Untersiemau/Coburg, Germany, 30° spray angle, 0.2 mm bore, operated with 5 bar nitrogen). The reaction mixture is heated at 100° C. for three hours with vigorous stirring, then cooled to room temperature before being analyzed.

Example 5

Added to 100 g of a hydrophilic silica having a specific surface area of 200 m$^2$/g, determined by the BET method in accordance with DIN 66131 and 66132 (available under the name HDK® N20 from Wacker Chemie AG, Munich, Germany) under a nitrogen atmosphere, by jetting through a two-fluid nozzle (hollow cone nozzle, model 121, from Düsen-Schlick GmbH, D-96253 Untersiemau/Coburg, Germany, 30° spray angle, 0.1 mm bore, operated with 5 bar nitrogen) are 3.75 g of water. Added subsequently in a similar way are 21 g of hexadecyltrimethoxysilane (hollow cone nozzle, model 121, from Düsen-Schlick GmbH, D-96253 Untersiemau/Coburg, Germany, 30° spray angle, 0.2 mm bore, operated with 5 bar nitrogen). The reaction mixture is heated at 100° C. for three hours with vigorous stirring, then cooled to room temperature before being analyzed.

Example 6

Added to 100 g of a hydrophilic silica having a specific surface area of 200 m$^2$/g, determined by the BET method in accordance with DIN 66131 and 66132 (available under the name HDK® N20 from Wacker Chemie AG, Munich, Germany) under a nitrogen atmosphere, by jetting through a two-fluid nozzle (hollow cone nozzle, model 121, from Düsen-Schlick GmbH, D-96253 Untersiemau/Coburg, Germany, 30° spray angle, 0.1 mm bore, operated with 5 bar nitrogen) is a mixture consisting of 1.26 g of ammonia and 3.78 g of water. Added subsequently in a similar way is a mixture of 18.4 g of octadecyltrimethoxysilane and 15 g of toluene (hollow cone nozzle, model 121, from Düsen-Schlick GmbH, D-96253 Untersiemau/Coburg, Germany, 30° spray angle, 0.2 mm bore, operated with 5 bar nitrogen). The reaction mixture is heated at 120° C. for three hours with vigorous stirring, then cooled to room temperature before being analyzed.

Example 7

Added to 100 g of a hydrophilic silica having a specific surface area of 200 m$^2$/g, determined by the BET method in accordance with DIN 66131 and 66132 (available under the name HDK® N20 from Wacker Chemie AG, Munich, Germany) under a nitrogen atmosphere, by jetting through a two-fluid nozzle (hollow cone nozzle, model 121, from Düsen-Schlick GmbH, D-96253 Untersiemau/Coburg, Germany, 30° spray angle, 0.1 mm bore, operated with 5 bar nitrogen) is a mixture consisting of 0.28 g of ammonia and 3.9 g of water. Added subsequently in a similar way is a mixture of 18.6 g of octadecyltrimethoxysilane and 15 g of toluene (hollow cone nozzle, model 121, from Düsen-Schlick GmbH, D-96253 Untersiemau/Coburg, Germany, 30° spray angle, 0.2 mm bore, operated with 5 bar nitrogen). The reaction mixture is heated at 120° C. for three hours with vigorous stirring, then cooled to room temperature before being analyzed.

Example 8

Added to 100 g of a hydrophilic silica having a specific surface area of 200 m$^2$/g, determined by the BET method in accordance with DIN 66131 and 66132 (available under the name HDK® N20 from Wacker Chemie AG, Munich, Germany) under a nitrogen atmosphere, by jetting through a two-fluid nozzle (hollow cone nozzle, model 121, from Düsen-Schlick GmbH, D-96253 Untersiemau/Coburg, Germany, 30° spray angle, 0.1 mm bore, operated with 5 bar nitrogen) is a mixture consisting of 1.40 g of ammonia and 5.03 g of water. Added subsequently in a similar way are 21.9 g of tetradecyltrimethoxysilane (hollow cone nozzle, model 121, from Düsen-Schlick GmbH, D-96253 Untersiemau/Coburg, Germany, 30° spray angle, 0.2 mm bore, operated with 5 bar nitrogen). The reaction mixture is heated at 120° C. for three hours with vigorous stirring, then cooled to room temperature before being analyzed.

Example 9

Added to 100 g of a hydrophilic silica having a specific surface area of 200 m²/g, determined by the BET method in accordance with DIN 66131 and 66132 (available under the name HDK® N20 from Wacker Chemie AG, Munich, Germany) under a nitrogen atmosphere, by jetting through a two-fluid nozzle (hollow cone nozzle, model 121, from Düsen-Schlick GmbH, D-96253 Untersiemau/Coburg, Germany, 30° spray angle, 0.1 mm bore, operated with 5 bar nitrogen) is a mixture consisting of 0.73 g of ammonia and 4.96 g of water. Added subsequently in a similar way are 21.9 g of tetradecyltrimethoxysilane (hollow cone nozzle, model 121, from Düsen-Schlick GmbH, D-96253 Untersiemau/Coburg, Germany, 30° spray angle, 0.2 mm bore, operated with 5 bar nitrogen). The reaction mixture is heated at 120° C. for three hours with vigorous stirring, then cooled to room temperature before being analyzed.

Example 10

Added to 60 g of a hydrophilic silica having a specific surface area of 50 m²/g, determined by the BET method in accordance with DIN 66131 and 66132 (available under the name HDK® N20 from Wacker Chemie AG, Munich, Germany) under a nitrogen atmosphere, by jetting through a two-fluid nozzle (hollow cone nozzle, model 121, from Düsen-Schlick GmbH, D-96253 Untersiemau/Coburg, Germany, 30° spray angle, 0.1 mm bore, operated with 5 bar nitrogen) is a mixture consisting of 1.2 g of triethylamine and 0.75 g of water. Added subsequently in a similar way are 2.4 g of methacryloyloxypropyltrimethoxysilane (hollow cone nozzle, model 121, from Düsen-Schlick GmbH, D-96253 Untersiemau/Coburg, Germany, 30° spray angle, 0.2 mm bore, operated with 5 bar nitrogen). The reaction mixture is subsequently heated at 120° C. in a drying oven under a nitrogen atmosphere for three hours, cooled to room temperature, and then analyzed.

Example 11

Added to 60 g of a hydrophilic silica having a specific surface area of 50 m²/g, determined by the BET method in accordance with DIN 66131 and 66132 (available under the name HDK® N20 from Wacker Chemie AG, Munich, Germany) under a nitrogen atmosphere, by jetting through a two-fluid nozzle (hollow cone nozzle, model 121, from Düsen-Schlick GmbH, D-96253 Untersiemau/Coburg, Germany, 30° spray angle, 0.1 mm bore, operated with 5 bar nitrogen) is a mixture consisting of 0.45 g of triethylamine and 0.75 g of water. Added subsequently in a similar way are 2.4 g of methacryloyloxypropyltrimethoxysilane (hollow cone nozzle, model 121, from Düsen-Schlick GmbH, D-96253 Untersiemau/Coburg, Germany, 30° spray angle, 0.2 mm bore, operated with 5 bar nitrogen). The reaction mixture is subsequently heated at 120° C. in a drying oven under a nitrogen atmosphere for three hours, cooled to room temperature, and then analyzed.

TABLE 1

Experimental data for inventive examples 1-11

| Example | Specific surface area of metal oxide [m²/g] | Covering agent | Auxiliary | Amount of auxiliary [μmol] per m² of specific surface area of the metal oxide |
|---|---|---|---|---|
| 1 | 200 | Hexadecyltrimethoxysilane | NH$_3$(aq) | 5.4 |
| 2 | 200 | Hexadecyltrimethoxysilane | NH$_3$(aq) | 3.7 |
| 3 | 200 | Hexadecyltrimethoxysilane | NH$_3$(aq) | 1.9 |
| 4 | 200 | Hexadecyltrimethoxysilane | NH$_3$(aq) | 0.6 |
| 5 | 200 | Hexadecyltrimethoxysilane | NH$_3$(aq) | 0.0 |
| 6 | 200 | Octadecyltrimethoxysilane | NH$_3$(aq) | 3.7 |
| 7 | 200 | Octadecyltrimethoxysilane | NH$_3$(aq) | 0.8 |
| 8 | 200 | Tetradecyltrimethoxysilane | NH$_3$(aq) | 4.2 |
| 9 | 200 | Tetradecyltrimethoxysilane | NH$_3$(aq) | 2.2 |
| 10 | 50 | Methacryloyloxypropyl-trimethoxysilane | NEt$_3$ | 4.0 |
| 11 | 50 | Methacryloyloxypropyl-trimethoxysilane | NEt$_3$ | 1.5 |

NH$_3$(aq) = Aqueous ammonia solution
NEt$_3$ = Triethylamine

TABLE 2

Analytical data for inventive examples 1-11

| Example | % C [wt %] | Occupancy [μmol/m²] | % SiOH [%] | Extractable constituents [wt %] | $^{29}$Si CP/MAS T1 [%] | $^{29}$Si CP/MAS T2 [%] | $^{29}$Si CP/MAS T3 [%] | Viscosity of dispersion [Pa * s] |
|---|---|---|---|---|---|---|---|---|
| 1 | 10.4 | 2.7 | 36 | 0.3 | 13 | 48 | 39 | 5.55 |
| 2 | 10.3 | 2.7 | 28 | 0.5 | 20 | 48 | 32 | 6.78 |
| 3 | 10.2 | 2.7 | 30 | 1.1 | 26 | 52 | 22 | 7.53 |

TABLE 2-continued

Analytical data for inventive examples 1-11

| Example | % C [wt %] | Occupancy [μmol/m$^2$] | % SiOH [%] | Extractable constituents [wt %] | $^{29}$Si CP/MAS T1 [%] | $^{29}$Si CP/MAS T2 [%] | $^{29}$Si CP/MAS T3 [%] | Viscosity of dispersion [Pa * s] |
|---|---|---|---|---|---|---|---|---|
| 4 | 11.0 | 2.9 | 30 | 0.8 | 42 | 46 | 13 | 8.57 |
| 5 | 9.7 | 2.5 | 61 | 4.9 | 48 | 52 | 0 | 6.92 |
| 6 | 9.7 | 2.2 | 46 | 2.2 | 18 | 53 | 29 | 4.69 |
| 7 | 10.3 | 2.4 | 48 | 2.8 | 22 | 50 | 28 | 5.22 |
| 8 | 10.0 | 3.0 | 28 | 1.0 | 20 | 45 | 35 | 8.05 |
| 9 | 9.7 | 2.9 | 27 | 1.4 | 24 | 47 | 29 | 8.35 |
| 10 | 1.3 | 3.1 | 68 | 0.1 | 17 | 61 | 22 | 3.60 |
| 11 | 1.2 | 2.9 | 68 | 0.1 | 43 | 48 | 10 | 4.22 |

What is claimed is:

1. A modified silica, modified with one or more modifying groups having the formula:

$$RSi(OX)(OX')O_{1/2} \quad (T1),$$

$$R'Si(OX'')(O_{1/2})_2 \quad (T2), \text{ and}$$

$$R''Si(O_{1/2})_3 \quad (T3),$$

where R, R', R'' are each independently an aliphatic or aromatic hydrocarbon radical having 1 to 24 C atoms, and X, X' and X'' are each independently hydrogen or an aliphatic or aromatic hydrocarbon radical having 1 to 24 C atoms and wherein the R, R', R'', X, X' and X'' radicals are identical or different, the fraction of T1 groups on the surface of the modified silica, based on the sum of T1+T2+T3, is at least 15%, or the fraction of T1 groups on the surface of the modified silica is greater than the fraction of T3 groups on the surface of the modified silica, determined by NMR spectroscopy in $^{29}$Si CP/MAS mode, and where the fraction of the modified silica that is extractable with solvents is not more than 15 wt %.

2. The modified silica of claim 1, wherein the radicals R, R', and R'' comprise alkyl or aryl radicals.

3. The modified silica of claim 1, wherein the silica comprises fumed silica.

4. The modified silica of claim 2, wherein the silica comprises fumed silica.

5. The modified silica of claim 1, wherein the degree of occupancy of the modifying groups is at least 2 μmol/m$^2$ of the surface area of the modified silica.

6. The modified silica of claim 2, wherein the degree of occupancy of the modifying groups is at least 2 μmol/m$^2$ of the surface area of the modified silica.

7. The modified silica of claim 3, wherein the degree of occupancy of the modifying groups is at least 2 μmol/m$^2$ of the surface area of the modified silica.

8. A method for surface-modifying a silica, to produce a modified silica of claim 1, comprising:

first, intensively mixing a particulate silica with a modifying agent, and then reacting the particulate silica with the modifying agent in a gas phase, and subsequently purifying a modified particulate silica by removing excess modifying agent and byproducts, where the modifying agent comprises a silane of the formula RSiZ$_3$, R$_2$SiZ$_2$ and/or R$_3$SiZ, where Z is a group reactive with surface silanol groups, R is a hydrocarbon radical having 1 to 24 C atoms, where 0.5 to 7 μmol of modifying agent per m$^2$ of specific surface area of the particulate silica to be modified are used for the modification, and where, in the reacting of the particulate silica with the modifying agent, one or more auxiliaries are added in an amount of less than 3 μmol per m$^2$ of the surface area of the silica to be modified.

9. The method of claim 8, wherein Z comprises at least one reactive group selected from the group consisting of hydroxyl, halogen, amine radicals, OR$^X$, OC(O)R$^X$, O(CH$_2$)$_m$OH or O(CH$_2$)$_m$OR$^X$, where R$^X$ is a hydrocarbon radical having 1 to 24 C atoms.

10. The method of claim 8, wherein at least a portion of the one or more auxiliaries are added to the particulate silica prior to intensively mixing the particulate silica with modifying agent.

11. The method of claim 8, wherein at least one auxiliary is a basic substance.

12. A method of modifying the rheological properties of a liquid medium, comprising dispersing a modified silica of claim 1 in the liquid medium.

13. The method of claim 12, wherein the liquid medium comprises an organic liquid.

14. A method of modifying the rheological properties of a liquid medium, comprising dispersing a modified silica prepared by the method of claim 8 in the liquid medium.

* * * * *